United States Patent

Muramoto et al.

[11] Patent Number: 5,900,426
[45] Date of Patent: May 4, 1999

[54] BENZOTHIAZOLE DERIVATIVES

[75] Inventors: Hiroki Muramoto; Kiyoshi Fukuda, both of Ono; Taisuke Hasegawa, Katoh-gun; Kaoru Okamoto, Katoh-gun; Takayuki Kotani, Katoh-gun, all of Japan

[73] Assignee: Nippon Zoki Pharmaceutical Co., Ltd., Osaka, Japan

[21] Appl. No.: 08/624,746

[22] Filed: Mar. 27, 1996

[30] Foreign Application Priority Data

Mar. 28, 1995 [JP] Japan .................................. 7-096300

[51] Int. Cl.⁶ ...................... A61K 31/415; C07D 277/64
[52] U.S. Cl. ........................ 514/367; 548/178; 548/180
[58] Field of Search ..................... 548/178, 180; 514/367

[56] References Cited

U.S. PATENT DOCUMENTS

| 3,852,298 | 12/1974 | Wagner et al. | 260/304 |
| 4,294,839 | 10/1981 | Doll et al. | 424/263 |
| 5,091,280 | 2/1992 | Yamaguchi et al. | 430/138 |

FOREIGN PATENT DOCUMENTS

| 0 030 632 A2 | 6/1981 | European Pat. Off. |
| 388682 | 9/1990 | European Pat. Off. |
| 472053 | 8/1994 | European Pat. Off. |
| 37 19 355 A1 | 12/1987 | Germany |
| 3719355 | 12/1987 | Germany |
| 53-71071 | 6/1978 | Japan |
| 59-36670 | 2/1984 | Japan |
| 4-128722 | 4/1992 | Japan |
| WO 92/0338 | 3/1992 | WIPO |

OTHER PUBLICATIONS

Gualtiere et al., J. med. Chem., 14(6), 546–49, Jul. 1971.
Chemical Abstract, vol. 112, No. 25, Jun. 18, 1990, abstract No. 35229b.
Chemical Abstract, vol. 86, No. 23, Jun. 6, 1977, abstract No. 171335t.
Chemical Abstract, vol. 78, No. 23, Jun. 11, 1973, abstract No. 147860z.
Chemical Abstract, vol. 75, No. 3, Jul. 19, 1971, abstract No. 19402c.
Chemical Abstract, vol. 75, No. 1, Jul. 5, 1971, abstract No. 6008d.
Chemical Abstract, vol. 72, No. 10, Mar. 9, 1970, abstract No. 45003f.
Chemical Abstract, vol. 75, No. 5, Aug. 2, 1971, abstract No. 35861g.
Chemical Abstracts, vol. 116, No. 21, May 25, 1992, abstraction No. 214443j.

*Primary Examiner*—Johann Richter
*Assistant Examiner*—Laura R. Cross
*Attorney, Agent, or Firm*—Fisher, Christen & Sabol

[57] ABSTRACT

Benzothiazole derivatives, pharmaceutically acceptable salts thereof, and therapeutic agents containing said compounds as an effective component possess a lipid lowering activity and are useful pharmaceuticals for the treatment of hyperlipemia. The lipid lowering agents are of the formula:

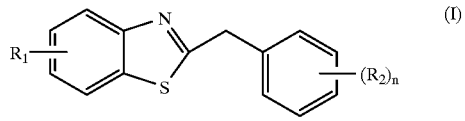

(I)

wherein $R_1$ is halogen, trifluoromethyl, acetamido or $-OX_1$; $X_1$ is hydrogen, alkyl or acyl; $R_2$ is hydrogen, halogen, alkyl, hydroxyalkyl, trifluoromethyl, nitro, amino which may be substituted with alkyl or acyl, carboxy which may be esterified with alkyl, or $-OX_2$; $X_2$ is hydrogen, alkyl, acyl, carboxyalkyl which may be esterified with alkyl; n is an integer from 1 to 3 denoting the number of substituents $R_2$; and plural $R_2$ may be the same or different when n is 2 or 3; with the proviso that $R_1$ is a group other than halogen when $R_2$ is hydrogen. The benzothiazole derivatives and their pharmaceutically acceptable salts significantly decrease cholesterol, triglyceride and low-density lipoprotein in blood.

20 Claims, No Drawings

BENZOTHIAZOLE DERIVATIVES

FIELD OF THE INVENTION

The present invention relates to novel benzothiazole derivatives and pharmaceutically acceptable salts thereof, which are useful as a medicine.

BACKGROUND OF THE INVENTION

Lipids such as cholesterol, triglycerides, phospholipids and free fatty acids are present in blood. Many kinds of diseases are caused by the abnormal increase or unbalance of such lipids. For instance, hyperlipemia is not only the direct cause of arteriosclerosis but also causes various symptoms such as abnormal glucometabolism, ischemic heart diseases, and the like.

Thus, the present inventors have conducted a study concerning novel compounds having a beneficial lipid lowering activity. As a result, they have found that the novel benzothiazole derivatives of the present invention have an excellent pharmacological activity whereby the present invention has been achieved.

SUMMARY OF THE INVENTION

The benzothiazole derivatives and their pharmaceutically acceptable salts of the present invention exhibit unexpectedly superior lipid lowering activity. The derivatives and their salts substantially reduce cholesterol, triglyceride and low-density lipoprotein in the blood. The compounds of the present invention include benzothiazole derivatives represented by the general formula (I) or pharmaceutically acceptable salts of the derivatives represented by the general formula (I):

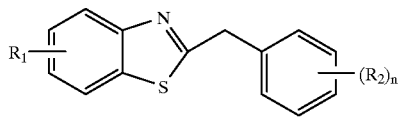
(I)

wherein
  $R_1$ is halogen, alkyl, trifluoromethyl, acetamido or —$OX_1$;
  $X_1$ is hydrogen, alkyl or acyl;
  $R_2$ is hydrogen, halogen, alkyl, hydroxyalkyl, trifluoromethyl, nitro, amino which may be substituted with alkyl or acyl, carboxy which may be esterified with alkyl, or —$OX_2$;
  $X_2$ is hydrogen, alkyl, acyl, carboxyalkyl which may be esterified with alkyl;
  and n is an integer from 1 to 3 denoting the number of substituents $R_2$;
  and plural $R_2$ may be the same or different when n is 2 or 3;
with the proviso that $R_1$ is a group other than chloro when $R_2$ is hydrogen.

The present invention also provides pharmaceutical compositions containing at least one of the derivatives of formula (I) or at least one salt thereof in a pharmaceutically acceptable amount.

The compounds and pharmaceutical compositions of the present invention may be used in pharmaceutically effective amounts to treat and prevent hyperlipemia.

DETAILED DESCRIPTION OF THE INVENTION

The present invention provides novel benzothiazole derivatives and pharmaceutically acceptable salts thereof, which have a lipid lowering activity and are useful as a medicine.

The compounds of the present invention include benzothiazole derivatives represented by the following formula (I) and pharmaceutically acceptable salts of the derivatives of formula (I):

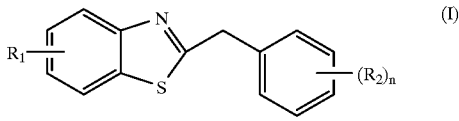
(I)

wherein
  $R_1$ is halogen, alkyl, trifluoromethyl, acetamido or —$OX_1$;
  $X_1$ is hydrogen, alkyl or acyl;
  $R_2$ is hydrogen, halogen, alkyl, hydroxyalkyl, trifluoromethyl, nitro, amino which may be substituted with alkyl or acyl, carboxy which may be esterified with alkyl, or —$OX_2$;
  $X_2$ is hydrogen, alkyl, acyl, carboxyalkyl which may be esterified with alkyl;
  and n is an integer from 1 to 3 denoting the number of substituents $R_2$;
  and plural $R_2$ may be the same or different when n is 2 or 3;
with the proviso that $R_1$ is a group other than chloro when $R_2$ is hydrogen.

In the above-mentioned general formula (I), $R_1$ is halogen such as fluorine, chlorine, bromine and iodine; a linear or branched alkyl having 1 to 6 carbon atoms such as methyl, ethyl, propyl, isopropyl, butyl, isobutyl, sec-butyl, t-butyl, pentyl, isopentyl, neopentyl, hexyl and dimethylbutyl; trifluoromethyl; acetamide; or —$OX_1$ wherein $X_1$ is: hydrogen; halogen such as fluorine, chlorine, bromine and iodine; a linear or branched alkyl having 1 to 6 carbon atoms such as methyl, ethyl, propyl, isopropyl, butyl, isobutyl, sec-butyl, t-butyl, pentyl, isopentyl, neopentyl, hexyl and dimethylbutyl; or a liner or branched acyl having 1 to 6 carbon atoms such as formyl, acetyl, propionyl, butyryl, isobutyryl, valeryl, isovaleryl, pivaloyl, and hexanoyl.

$R_2$ is hydrogen; halogen such as fluorine, chlorine, bromine and iodine; a linear or branched alkyl having 1 to 6 carbon atoms such as methyl, ethyl, propyl, isopropyl, butyl, isobutyl, sec-butyl, t-butyl, pentyl, isopentyl, neopentyl, hexyl and dimethylbutyl; a linear or branched hydroxyalkyl wherein the alkyl has 1 to 6 carbon atoms such as methyl, ethyl, propyl, isopropyl, butyl, isobutyl, sec-butyl, t-butyl, pentyl, isopentyl, neopentyl, hexyl and dimethylbutyl; trifluoromethyl; nitro; amino which may be substituted with 1 or 2 linear or branched alkyls having 1 to 6 carbon atoms such as methyl, ethyl, propyl, isopropyl, butyl, isobutyl, sec-butyl, t-butyl, pentyl, isopentyl, neopentyl, hexyl and dimethylbutyl or with 1 or 2 linear or branched acyls having 1 to 6 carbon atoms such as formyl, acetyl, propionyl, butyryl, isobutyryl, valeryl, isovaleryl, pivaloyl, and hexanoyl; carboxy which may be esterified with a linear or branched alkyl having 1 to 6 carbon atoms such as methyl, ethyl, propyl, isopropyl, butyl, isobutyl, sec-butyl, t-butyl, pentyl, isopentyl, neopentyl, hexyl and dimethylbutyl; or —$OX_2$ wherein $X_2$ is: hydrogen; halogen such as fluorine, chlorine, bromine and iodine; a linear or branched alkyl having 1 to 6 carbon atoms such as methyl, ethyl, propyl, isopropyl, butyl, isobutyl, sec-butyl, t-butyl, pentyl, isopentyl, neopentyl, hexyl and dimethylbutyl; a linear or branched acyl having 1 to 6 carbon atoms such as formyl, acetyl, propionyl, butyryl, isobutyryl, valeryl, isovaleryl, pivaloyl, and hexanoyl; or carboxy-alkyl($C_{1-6}$) which may be esterified with a linear or branched alkyl having 1 to 6 carbon atoms such as methyl, ethyl, propyl, isopropyl, butyl, isobutyl, sec-butyl, t-butyl, pentyl, isopentyl, neopentyl, hexyl and dimethylbutyl.

The compounds of the present invention may, for example, be produced in accordance with several methods. For example, a benzothiazole having a substituent corresponding to $R_1$ is treated with a base such as n-butyllithium, t-butyllithium or lithium diisopropylamide at a low temperature. The resulting product is reacted with a compound such as a benzoic ester, benzoyl chloride, benzamide or benzonitrile, which has a substituent corresponding to $R_2$, to give a $R_1$-2-($R_2$-benzoyl)benzothiazole derivative.

In another method, the benzothiazole derivatives of the present invention may be produced by dissolving both a benzothiazole having a substituent corresponding to $R_1$ and a benzaldehyde having a substituent corresponding to $R_2$ in a mixture of water and acetic acid containing concentrated sulfuric acid. Then, to the reaction mixture, a solution of a reagent for producing acyl radicals, such as cerium sulfate, chromium sulfate, manganese sulfate, copper sulfate or iron sulfate, and t-butylhydroperoxide are simultaneously added to produce said benzothiazole derivative.

In producing the benzothiazole derivative of the present invention wherein $R_1$ and/or $R_2$ is hydroxy (i.e. $X_1$ and/or $X_2$ is hydrogen), a reactant compound having a hydroxy-protecting group such as (2-methoxyethoxy)methyl, benzyl or acetyl is used and reacted as mentioned above, and then the protecting group is removed to produce the intended benzothiazole derivative. For example, if $R_1$ is a hydroxy group, a benzothiazole having a protected hydroxy substituent corresponding to the position of $R_1$ is treated with a base such as n-butyllithium, t-butyllithium or lithium diisopropylamide at a low temperature. The resulting product is reacted with a compound such as a benzoic ester, benzoyl chloride, benzamide or benzonitrile, which has a substituent corresponding to $R_2$, to give a protected hydroxy-2-($R_2$-benzoyl)benzothiazole derivative. Then the protecting group is removed in conventional manner to produce the intended benzothiazole derivative.

Similarly, if $R_2$ is hydroxy, a benzothiazole having a substituent corresponding to $R_1$ is treated with a base such as n-butyllithium, t-butyllithium or lithium diisopropylamide at a low temperature. The resulting product is reacted with a compound such as a benzoic ester, benzoyl chloride, benzamide or benzonitrile, which has a protected hydroxy substituent corresponding to the position of $R_2$, to give a $R_1$-2-(protected hydroxy-benzoyl)benzothiazole derivative. Then the protecting group is removed in conventional manner to produce the intended benzothiazole derivative.

In using the other method, if $R_1$ is a hydroxy group the benzothiazole derivatives of the present invention may be produced by dissolving both a benzothiazole having a protected hydroxy substituent at the $R_1$ position and a benzaldehyde having a substituent corresponding to $R_2$ in a mixture of water and acetic acid containing concentrated sulfuric acid. Then, to the reaction mixture, a solution of a reagent for producing acyl radicals, such as cerium sulfate, chromium sulfate, manganese sulfate, copper sulfate or iron sulfate, and t-butylhydroperoxide are simultaneously added to produce said benzothiazole derivative. Then the protecting group is removed in conventional manner to produce the intended benzothiazole derivative. In using this method when $R_2$ is hydroxy, a benzaldehyde having a protected hydroxy substituent at the corresponding position of $R_2$ may be used as a reactant for reaction with the dissolved benzothiazole having a substituent corresponding to $R_1$.

The benzothiazole derivatives wherein $R_1$ and/or $R_2$ is hydroxy (i.e. $X_1$ and/or $X_2$ is hydrogen) may be used to produce the other benzothiazole derivatives wherein $R_1$ is —$OX_1$ and/or $R_2$ is —$OX_2$. For example, such benzothiazole derivatives may be produced by a conventional acylation of the $R_1$ and/or $R_2$ hydroxy group. Exemplary synthesis reactions which may be used are: a condensation reaction between the above benzothiazole derivative wherein $R_1$ or $R_2$ is hydroxy and a carbonic anhydride such as acetic anhydride or a halogenated compound such as acetyl chloride, or a reaction of a carboxylic acid and a dehydrating-condensing agent such as dicyclohexylcarbodiimide (DCC).

To produce a benzothiazole derivative wherein $R_2$ is carboxy or wherein $X_2$ is carboxyalkyl, such benzothiazole derivative maybe produced by hydrolysis of its ester form.

The novel compounds of the present invention include the pharmaceutically acceptable salts of the benzothiazole derivatives represented by the above-given general formula (I). Exemplary salts of the present invention are acid addition salts of the benzothiazole derivatives of general formula (I) with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, or sulfanilic acid. Other salts of the present invention include salts of the benzothiazole derivatives of general formula (I) with: a) an alkali metal such as sodium and potassium, b) an alkaline-earth metal such as calcium, magnesium and barium, c) other metals such as aluminum, or d) a base such as ammonia a nd organic amines.

The pharmaceutically accept able salts may be manufactured, by convent ion al methods, starting from the benzothiazole derivatives of the present invention in a free state or free form, or by conversion from one salt to another salt.

When there are stereoisomers such as cis-trans isomers, optical isomers and conformational isomers for the compounds of the present invention, or when the compounds exist as hydrates, the present invention includes any and all of such stereoisomers and hydrates.

The compounds of the present invention prepared as described above may be purified by conventional means such as distillation, chromatography and recrystallization. The compounds may be identified by means of, for example, elementary analysis, melting point measurement, infrared (IR), nuclear magnetic resonance (NMR), ultraviolet (UV), and mass spectroscopy (MS).

The compounds of the present invention, which include the benzothiazole derivatives and their pharmaceutically acceptable salts, can be made into pharmaceutical preparations by combining one or more of the compounds with at least one pharmaceutically acceptable carrier or diluent. The derivatives and their salts can be made into various types of preparations by known methods. The compounds of the present invention can be made into solid, semisolid, liquid or aerosol formulations for administration by oral or parenteral means.

The compounds of the present invention may be used either solely or jointly in pharmaceutically effective amounts for treating animals or humans. In preparing the preparations, the benzothiazole derivatives of the present invention may be used in the form of their pharmaceutically acceptable salts. The compounds of the invention can be used either solely or jointly together in pharmaceutically effective amounts with pharmaceutically effective amounts of other pharmaceutically-active components in pharmaceutical compositions or preparations.

In the case of parenteral administration using injections, for example, it is possible to prepare solutions or suspensions of one or more compounds of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, etc. Adjustment of the pH and isotonicity of the solution or suspension may be accomplished in known manner.

In the case of preparations for oral administration, one or more of the compounds of the present invention alone or together with commonly-used pharmaceutically acceptable excipients in pharmaceutically acceptable amounts such as a suitable pharmaceutically acceptable additive or carrier (e.g. lactose, mannitol, corn starch, potato starch, crystalline cellulose, etc.) may be mixed with one or more pharmaceutically acceptable: (1) binders such as crystalline cellulose, cellulose derivatives, gum arabicum, corn starch, gelatin, etc., (2) disintegrating agents such as corn starch, potato starch, carboxymethylcellulose, potassium carboxymethylcellulose, etc., (3) lubricating agents such as talc, magnesium stearate, etc., and (4) other pharmaceutically acceptable excipients including pharmaceutically acceptable bulking agents, moisturizing agents, buffers, preservatives, perfumes and the like to obtain tablets, diluted powders, granules or capsules.

Alternatively, suppositories may be prepared by mixing at least one compound of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In case of inhalations or aerosol preparations, at least one compound of the present invention in the form of a liquid or minute powder can be filled up in an aerosol container with a gas or liquid spraying agent, and if desired, with one or more conventional adjuvants such as one or more pharmaceutically acceptable humidifying agents or dispersing agent. They can also be used as pharmaceuticals for a non-pressurized preparation such as in a nebulizer or an atomizer.

In order to make the compounds of the present invention into collyriums, they can be prepared as a solution or suspension together with an aqueous solvent such as sterile, purified water and physiological saline solution, or a non-aqueous solvent for injection. The collyriums may also include pharmaceutically acceptable preservants, sterilizing agents, pH adjusting agents, and the like.

It is also possible, depending upon the type of the disease, to prepare pharmaceutical preparations other than the above-mentioned ones such as ointments, poultices, etc. which are suitable for therapy depending upon the state of the patient and the type of disease.

The preferred dosage of the compound of the present invention varies depending upon the subject to be administered (age, body weight, symptoms, etc. of the patient), form of the preparation, method for the administration, treatment for the administration, etc. To achieve the desired result, the compound may be usually administered by the oral route with a daily dose of 2–2,000 mg, preferably 5–1,000 mg per day, to common adults.

In the case of parenteral administration such as by injection, the preferred dosage may be from one-third to one-tenth of the above-mentioned oral dosage because of the effects of absorption, etc. in the oral route.

The present invention is illustrated by the following examples wherein all parts, percentages and ratios are by weight, all temperatures are in ° C., and all reactions are conducted at about atmospheric pressure unless indicated to the contrary. The following examples include exemplary methods for manufacturing the compounds of the present invention. The compounds of the present invention were purified by common means such as distillation, chromatography and recrystallization and identified by means of, for example, elementary analysis, melting point measurement, IR, NMR, UV and MS:

EXAMPLE 1

This example illustrates the production of: 1) a benzothiazole reactant having a protected hydroxy group, 2) a benzoic ester reactant having a protected hydroxy group, and 3) a benzothiazole derivative which is the reaction product of the benzothiazole reactant and the benzoic ester reactant.

(1) Production of Protected Benzothiazole Reactant

A solution of 1 g of 6-hydroxybenzothiazole in dimethylformamide was dropped into a solution of 0.4 g of 60% sodium hydride in 3 ml of dimethylformamide at 0° C. After the mixture was stirred at room temperature for 1 hour, 0.75 ml of (2-methoxyethoxy)methylchloride was added dropwise into the mixture and the mixture was stirred for another 1 hour. NaCl was added to the reaction mixture and the mixture was extracted with ether. The extracts were dried over sodium sulfate and concentrated, and then the residue was purified by column-chromatography (hexane : ethyl acetate=5:1) to give 0.6 g of 6-[(2-methoxyethoxy)-methoxy]benzothiazole. $^{11}$H-NMR(CDCl$_3$): 3.38(s,3H), 3.58(m,2H), 3.87(m,2H), 7.22(dd,J=8.8,2.4 Hz,1H), 7.66(d, J=2.4 Hz,1H), 8.82(d,J=8.8 Hz,1H), 8.86(s,1H) IR(neat) cm$^{-1}$: 2927, 1674, 1475, 1230, 1103, 999 MS(EI) m/z: 239(M$^+$), 89, 59

(2) Production of Protected Benzoic Ester Reactant

Similar operations as in paragraph (1) above were carried out using 4-hydroxybenzoic ethyl ester. 1.4 g of 60% sodium hydride was washed with hexane and dissolved in 50 ml of dimethylformamide. A solution of 5 g of ethyl 4-hydroxybenzoate in dimethylformamide (50 ml) was added dropwise into this solution at 0° C. After the mixture was stirred at room temperature for 1 hour, 4.1 ml of (2-methoxyethoxy)methylchloride was added dropwise into the mixture and the mixture was stirred for another 1 hour. NaCl was added to the reaction mixture and the mixture was extracted with ether. The extracts were dried over sodium sulfate and concentrated, and then the residue was purified by distillation (135° C., 1 mmHg) to afford 7.0 g of ethyl 4-[(2-methoxyethoxy)methoxy]-benzoate. bp: 135° C. (1 mmHg) $^1$H-NMR(CDCl$_3$): 1.38(t,J=7.1 Hz,3H), 3.37(s,3H), 3.55(m,2H), 3.82(m,2H), 4.35(q,J=7.1 Hz,2H), 5.32(s,2H), 7.07(d,J=8.8 Hz,2H), 7.99(d,J=8.8 Hz,2H) IR(neat) cm$^{-1}$: 2981, 1713, 1606, 1276, 1104, 988 MS(EI) m/z: 254(M$^+$), 209, 179, 121, 89, 59

(3) Production of Benzothiazole Derivative With Protected Hydroxyl Groups By Reaction of Benzothiazole Reactant and Benzoic Ester Reactant A solution of 1.3 N of n-butyllithium in hexane (0.7 ml) was added to a solution of 220 mg of 6-[(2-methoxyethoxy) methoxy]benzothiazole (obtained as in paragraph 1 above) in 30 ml of tetrahydrofuran at −78° C. cooled by dry ice—acetone. The mixture was added dropwise into a solution of 234 mg of ethyl 4-[(2-methoxyethoxy)methoxy] benzoate (obtained as in paragraph 2 above) in tetrahydrofuran (3 ml) cooled by dry ice—acetone. NH$_4$Cl was added to the reaction mixture and the mixture was extracted with ether. The extracts were washed with water and dried over sodium sulfate. After being concentrated, the residue was recrystallized from ethyl acetate to yield 320 mg of 6-(2-methoxyethoxy)methoxy-2-{4-[(2-methoxyethoxy)methoxy]benzoyl}benzothiazole (Compound 1). mp: 46° C. $^1$H-NMR(CDCl$_3$): 3.38(s,3H), 3.38(s,3H), 3.58(m,4H), 3.86 (m,4H), 5.38(s,4H), 7.18(d,J=8.8 Hz,2H), 7.28(dd,J=9.1,2.2 Hz,1H), 7.67(d,J=2.2 Hz,1H), 8.10(d,J=9.1 Hz,1H), 8.59(d, J=8.8 Hz,2H) IR(KBr) cm$^{-1}$: 2877, 1598, 1488, 1214, 1117, 987 MS m/z: 447(M$^+$), 89, 59 Elementary analysis (C$_{22}$H$_{25}$NO$_7$S): Calculated (C=59.05,H=5.63,N=3.13); Found (C=59.15,H=5.58,N=2.93)

EXAMPLE 2

Reaction of a benzothiazole reactant and a benzoic ester reactant was carried out as in Example 1 to obtain the following compounds:

6-Methoxy-2-(4-methoxybenzoyl)benzothiazole (Compound 2) mp: 142° C. $^1$H-NMR(DMSO-d$_6$): 3.91(s, 6H), 7.17(d,J=8.9 Hz,2H), 7.26(dd,J=8.9,2.4 Hz,1H), 7.81 (d,J=2.4 Hz,1H), 8.16(d,J=8.9 Hz,1H), 8.54(d,J=8.9 Hz,2H) Elementary analysis (C$_{16}$H$_{13}$NO$_3$S): Calculated (C=64.20, H=4.38,N=4.68); Found (C=64.31,H=4.52,N=4.40)

6-[(2-Methoxyethoxy)methoxy]-2-(4-nitrobenzoyl)benzothiazole (Compound 3) mp: 143–144° C. $^1$H-NMR (DMSO-d$_6$): 3.22(s,3H,CH$_3$), 3.46–3.50(m,2H,CH$_2$), 3.76–3.80(m,2H,CH$_2$), 5.42(s,2H,CH$_2$), 7.37(dd,J=9.2,2.6 Hz,1H,Ar—H), 7.93(d,J=2.6 Hz,1H,Ar—H), 8.21(d,J=9.2 Hz,1H,Ar—H), 8.43(d,J=8.8 Hz,2H,Ar—H), 8.56(d,J=8.8 Hz,2H,Ar—H) IR(KBr) cm$^{-1}$: 1645(C=O), 1597, 1525 (NO$_2$), 1351(NO$_2$) MS m/z: 388(M$^+$) Elementary analysis (C$_{18}$H$_{16}$N$_2$O$_6$S): Calculated (C=55.66,H=4.15,N=7.21); Found (C=55.69,H=4.08,N=7.61)

6-[(2-Methoxyethoxy)methoxy]-2-(3-nitrobenzoyl)benzothiazole (Compound 4) mp: 85–86° C. $^1$H-NMR (DMSO-d$_6$): 3.22(s,3H,CH$_3$), 3.46–3.50(m,2H,CH$_2$), 3.76–3.80(m,2H,CH$_2$), 5.42(s,2H,CH$_2$), 7.37(d,J=9.0 Hz,1H,Ar—H), 7.90–7.96(m,2H,Ar—H), 8.22(d,J=9.0 Hz,1H,Ar—H), 8.58(d,J=7.6 Hz,1H,Ar—H), 8.81(d,J=7.6 Hz,1H,Ar—H), 9.21(s,1H,OH) IR(KBr) cm$^{-1}$: 1643 (C=O), 1527(NO$_2$), 1491, 1350(NO$_2$) MS m/z: 388(M$^+$) Elementary analysis (C$_{18}$H$_{16}$N$_2$O$_6$S): Calculated (C=55.66, H=4.15,N=7.21); Found (C=55.60,H=4.06,N=7.52)

6-[(2-Methoxyethoxy)methoxy]-2-(2-nitrobenzoyl)benzothiazole (Compound 5) mp: 89–90° C. $^1$H-NMR (DMSO-d$_6$): 3.21(s,3H,CH$_3$), 3.46–3.50(m,2H,CH$_2$), 3.76–3.80(m,2H,CH$_2$), 5.39(s,2H,CH$_2$), 7.29(dd,J=9.0,2.4 Hz,1H,Ar—H), 7.88–7.94(m,3H,Ar—H), 7.99–8.04(m,2H, Ar—H), 8.31(d,J=8.8 Hz,1H,Ar—H) IR(KBr) cm$^{-1}$: 1670 (C=O), 1603, 1525(NO$_2$), 1354(NO$_2$) MS m/z: 388(M$^+$) Elementary analysis (C$_{18}$H$_{16}$N$_2$O$_6$S): Calculated (C=55.66, H=4.15,N=7.21); Found (C=55.84,H=4.14,N=7.09)

2-(3-Fluorobenzoyl)-6-[(2-methoxyethoxy)methoxy]-benzothiazole (Compound 6) mp: 60–61° C. $^1$H-NMR (CDCl$_3$): 3.38(s,3H,CH$_3$), 3.56–3.64(m,2H,CH$_2$), 3.87–3.90(m,2H,CH$_2$), 5.38(s,2H,CH$_2$), 7.29(dd,J=9.2,2.6 Hz,1H,Ar—H), 7.36(ddd,J=8.4,8.4,2.4 Hz,1H,Ar—H), 7.53 (ddd,J=8.4,8.4,5.6 Hz,1H,Ar—H), 7.68(d,J=2.4 Hz,1H, Ar—H), 8.13(d,J=9.2 Hz,1H,Ar—H), 8.31(ddd,J=7.6,2.4, 2.4 Hz,1H,Ar—H), 8.36(d,J=7.6 Hz,1H,Ar—H) IR(KBr) cm$^{-1}$: 1637(C=O), 1605, 1583, 1497 MS m/z: 361(M$^+$) Elementary analysis (C$_{18}$H$_{16}$FN$_2$O$_6$S 0.6 EtOAc): Calculated (C=59.16,H=5.06,N=3.38); Found (C=59.32,H=5.45, N=3.78)

EXAMPLE 3

This example illustrates removal of hydroxy protecting groups to obtain a benzothiazole derivative in accordance with the present invention.

0.2 ml of trifluoroacetic acid was added to a solution of 4 g of the Compound 1 obtained in Example 1 in water-methanol. The mixture was stirred for 48 hours at 70° C. After the reaction was completed, methanol was evaporated and the crystals were collected by filtration and dried to give 2.3 g of 6-hydroxy-2-(4-hydroxybenzoyl)benzothiazole (Compound 7). mp: 46° C. $^1$H-NMR(aceton-d$_6$): 7.01(d,J= 8.9 Hz,2H), 7.18(dd,J=8.9,2.4 Hz,1H), 7.52(d,J=2.4 Hz,1H), 8.05(d,J=8.9 Hz,1H), 8.58(d,J=8.9 Hz,2H), 9.15(br,1H), 9.40(br,1H) IR(KBr) cm$^{-1}$: 3463, 1602, 1589, 1491, 1249, 1176, 1119, 875 MS m/z: 271(M$^+$), 243, 121 Elementary analysis (C$_{14}$H$_9$NO$_3$S 0.8 H$_2$O): Calculated (C=58.84,H= 3.74,N=4.90); Found (C=58.78,H=3.55,N=4.54)

EXAMPLE 4

The same reaction as used in Example 3 was carried out to remove the protecting groups of Compounds 3, 4, and 5 to give the following compounds 8, 9, and 10, respectively:

6-Hydroxy-2-(4-nitrobenzoyl)benzothiazole (Compound 8) mp: 238–239° C. $^1$H-NMR(DMSO-d$_6$): 7.16(dd,J=9.0,2.2 Hz,1H,Ar—H), 7.54(d,J=2.2Hz,2H,Ar—H), 8.10(d,J=9.0 Hz,1H,Ar—H), 8.43(d,J=8.8 Hz,2H,Ar—H), 8.57(d,J=8.8 Hz,2H,Ar—H), 10.47(brs,1H,OH) IR(KBr) cm$^{-1}$: 3464 (OH), 1641(C=O), 1603, 1518(NO$_2$), 1356(NO$_2$) MS m/z: 300(M$^+$) Elementary analysis (C$_{14}$H$_8$N$_2$O$_4$S 0.1 H$_2$O): Calculated (C=55.66,H=2.74,N=9.27); Found (C=55.45,H= 2.73,N=9.07)

6-Hydroxy-2-(3-nitrobenzoyl)benzothiazole (Compound 9) mp: >300° C. $^1$H-NMR(DMSO-d$_6$): 7.37(d,J=8.0 Hz,1H, Ar—H), 7.87(dd,J=8.6,8.0 Hz,1H,Ar—H), 8.07(d,J=8.6 Hz,1H,Ar—H), 8.52(d,J=8.0 Hz,1H,Ar—H), 8.70(d,J=8.0 Hz,1H,Ar—H), 9.10(s,1H,Ar—H), 10.92(brs,1H,OH) IR(KBr) cm$^{-1}$: 3422(OH), 1650(C=O), 1608, 1524(NO$_2$), 1498, 1355(NO$_2$), 1259 Elementary analysis (C$_{14}$H$_8$N$_2$O$_4$S 0.15 H$_2$O): Calculated (C=55.50,H=2.76,N=9.25); Found (C=55.74,H=2.65,N=9.00)

6-Hydroxy-2-(2-nitrobenzoyl)benzothiazole (Compound 10) mp: 265–266° C. (decomp.) $^1$H-NMR(DMSO-d$_6$): 7.37 (d,J=8.0 Hz,1H,Ar—H), 7.87(dd,J=8.6,8.0 Hz,1H,Ar—H), 8.07(d,J=8.6 Hz,1H,Ar—H), 8.52(d,J=8.0 Hz,1H,Ar—H), 8.70(d,J=8.0 Hz,1H,Ar—H), 9.10(s,1H,Ar—H), 10.92(brs, 1H,OH) IR(KBr) cm$^{-1}$: 3449(OH), 1663(C=O), 1613, 1557, 1524(NO$_2$), 1497, 1462, 1349(NO$_2$), 1271, 1250, 1205 MS m/z: 300(M$^+$) Elementary analysis (C$_{14}$H$_8$N$_2$O$_4$S 0.55 H$_2$O): Calculated (C=59.38,H=3.24,N=4.95); Found (C=59.70,H=3.42,N=4.61)

EXAMPLE 5

This example illustrates the use of benzothiazole derivatives having a hydroxy substituent for the production of other benzothiazole derivatives of the present invention.

4 ml of acetic anhydride was added to a solution of 2.3 g of the compound 7 hydrochloride in 40 ml of pyridine and the mixture was stirred overnight. The reaction mixture was poured into 50 ml of ice water and the resulting precipitate was separated. The solid was recrystallized from benzene to yield 1.8 g of 6-acetoxy-2-(4-acetoxybenzoyl)benzothiazole (Compound 11). mp: 183° C. $^1$H-NMR(DMSO-d$_6$): 8.52(d, J=8.7 Hz,2H), 8.33(d,J=8.9 Hz,1H), 8.12(d,J=2.2 Hz,1H), 7.47(dd,J=8.9,2.2 Hz,1H), 7.42(d,J=8.7 Hz,2H), 2.35(s,3H), 2.34(s,3H) IR(KBr) cm$^{-1}$: 1763, 1493, 1186, 1161, 872 MS m/z: 355(M$^+$), 313, 271, 243, 121, 43 Elementary analysis (C$_{22}$H$_{25}$NO$_7$S): Calculated (C=60.84,H=3.69,N=3.94); Found (C=60.98,H=3.63,N=3.55)

EXAMPLE 6

This example illustrates production of a benzothiazole derivative of the present invention using a benzothiazole reactant having a substituent corresponding to R$_1$ and a benzaldehyde reactant having a substituent corresponding to R$_2$ 4.37 g of 6-hydroxybenzothiazole and 11.0 g of 4-hydroxybenzaldehyde were dissolved in a mixed solvent of 22 ml of water and 66 ml of acetic acid containing 1.3 ml of concentrated sulfuric acid and the mixture was cooled at 0° C. 65 ml of an aqueous solution containing 25.7 g of FeSO$_4$ 7H$_2$O and 3 equivalents of t-butylhydroperoxide were separately added dropwise into the mixture with stirring. After the mixture was stirred for 1 hour, the crystals were collected by filtration, dissolved in ethyl acetate and washed with water. The organic layer was dried over mirabilite and concentrated. Then the residue was recrystallized from ethanol-water (1:1) to yield 5.50 g of the Compound 7.

EXAMPLE 7

A benzothiazole reactant which may have a substituent corresponding to R$_1$ and a benzaldehyde reactant which may have a substituent corresponding to R$_2$ may be reacted as in Example 6 to give the following compounds:

2-(4-Hydroxybenzoyl)-6-methoxybenzothiazole (Compound 12) mp: 193–194 ° C. $^1$H-NMR(DMSO-d$_6$): 3.90(s,1H,CH$_3$), 6.97(d,J=8.6 Hz,2H,Ar—H), 7.26(dd,J=9.0,2.0 Hz,1H,Ar—H), 7.81(d,J=2.0 Hz,1H,Ar—H), 8.16(d,J=9.0 Hz,1H,Ar—H), 8.16(d,J=8.6 Hz,2H,Ar—H), 10.68 (brs,1H,OH) IR(KBr) cm$^{-1}$: 3386(OH), 1603(C=O), 1578, 1491, 1254 MS m/z: 285(M$^+$) Elementary analysis (C$_{15}$H$_{11}$NO$_3$S): Calculated (C=63.14,H=3.89,N=4.91); Found (C=63.22,H=3.88,N=4.92)

6-Hydroxy-2-(4-methoxybenzoyl)benzothiazole (Compound 13) mp: 190–191° C. (decomp.) $^1$H-NMR (DMSO-d$_6$): 3.90(s,3H,CH$_3$), 7.10–7.20(m,3H,Ar—H), 7.51(s,1H,Ar—H), 8.09(d,J=9.0 Hz,1H,Ar—H), 8.53(d,J=8.6 Hz,1H,Ar—H), 10.34(brs,1H,OH) IR(KBr) cm$^{-1}$: 3340 (OH), 1601(C=O), 1489, 1257 MS m/z: 285(M$^+$) Elementary analysis (C$_{15}$H$_{11}$NO$_3$S): Calculated (C=63.14,H=3.89, N=4.91); Found (C=63.23,H=3.98,N=4.51)

2-(4-Hydroxybenzoyl)benzothiazole (Compound 14) mp: 173–174° C. $^1$H-NMR(DMSO-d$_6$): 6.99(d,J=8.6 Hz,2H, Ar—H), 7.60–7.72(m,2H,Ar—H), 8.28(dd,J=7.0,7.0 Hz,2H,Ar—H), 8.28(dd,J=7.0,7.0 Hz,2H,Ar—H), 8.49(d,J=8.6 Hz,1H,Ar—H), 10.73(brs,1H,OH) IR(KBr) cm$^{-1}$: 3304 (OH), 1572(C=O), 1485, 1288 MS m/z: 255(M$^+$) Elementary analysis (C$_{14}$H$_9$NO$_2$S): Calculated (C=65.87,H=3.55, N=5.49); Found (C=65.94,H=3.53,N=5.15)

2-Benzoyl-6-hydroxybenzothiazole (Compound 15) mp: 146–147° C. $^1$H-NMR(DMSO-d$_6$): 7.14(dd,J=11.4,1.8 Hz,1H,Ar—H), 7.52(d,J=1.8 Hz,1H,Ar—H), 7.63(dd,J=8.0, 7.2 Hz,2H,Ar—H), 8.10(tt,J=7.2,1.0 Hz,1H,Ar—H), 8.42 (dd,J=8.0,1.0 Hz,2H,Ar—H), 10.39(brs,1H,OH) IR(KBr) cm$^{-1}$: 3327(OH), 1610(C=O), 1468, 1255 MS m/z: 255 (M$^+$) Elementary analysis (C$_{14}$H$_9$NO$_2$S 0.1 H$_2$O): Calculated (C=65.40,H=3.60,N=5.45); Found (C=65.13,H=3.58,N 5.32)

2-(2,4-Dihydroxybenzoyl)-6-methoxybenzothiazole (Compound 16) mp: 220–221° C. (decomp.) $^1$H-NMR (DMSO-d$_6$): 3.90(s,3H,CH$_3$), 6.36(s,1H,Ar—H), 6.53(d,J=7.8 Hz,1H,Ar—H), 7.27(d,J=8.6 Hz,1H,Ar—H), 7.83(s,1H, Ar—H), 8.17(d,J=8.6 Hz,1H,Ar—H), 9.06(d,J=7.8 Hz,1H, Ar—H), 11.15(brs,1H,OH), 12.36(brs,1H,OH) IR(KBr) cm$^{-1}$: 3427(OH), 1633(C=O), 1485, 1230 MS m/z: 301 (M$^+$) Elementary analysis (C$_{15}$H$_{11}$NO$_4$S 0.1 H$_2$O): Calculated (C=59.44,H=3.72,N=4.62); Found (C=59.39,H=3.61, N=4.37)

2-(2,4-Dihydroxybenzoyl)-6-hydroxybenzothiazole (Compound 17) mp: 239–240° C. (decomp.) $^1$H-NMR (DMSO-d$_6$): 6.34(s,1H,Ar—H), 6.51(d,J=9.0 Hz,1H,Ar—H), 7.13(dd,J=9.0,2.4 Hz,1H,Ar—H), 7.51(d,J=2.2 Hz,1H, Ar—H), 8.09(d,J=9.0 Hz,1H,Ar—H), 9.05(d,J=9.0 Hz,1H, Ar—H), 10.40(brs,1H,OH), 12.42(brs,1H,OH) IR(KBr) cm$^{-1}$: 3388(C=O), 3302(C=O), 1633(C=O), 1606, 1491, 1254 MS m/z: 287(M$^+$) Elementary analysis (C$_{14}$H$_9$NO$_4$S ⅓ H$_2$O): Calculated (C=57.33,H=3.32,N=4.78); Found (C=57.14,H=3.25,N=4.54)

2-(3-Hydroxybenzoyl)-6-methoxybenzothiazole (Compound 18) mp: 174–175° C. $^1$H-NMR(DMSO-d$_6$): 3.90(s,3H,CH$_3$), 7.14(d,J=7.8 Hz,1H,Ar—H), 7.28(d,J=8.8 Hz,1H,Ar—H), 7.43(dd,J=7.8,7.8 Hz,1H,Ar—H), 7.80–7.90(m,2H,Ar—H), 7.93(d,J=7.8 Hz,1H,Ar—H), 8.18 (d,J=8.8 Hz,1H,Ar—H), 9.92(brs,1H,OH) IR(KBr) cm$^{-1}$: 3423(OH), 1585(C=O), 1489, 1454, 1263, 1223 MS m/z: 285(M$^+$) Elementary analysis (C$_{15}$H$_{11}$NO$_3$S): Calculated (C=63.14,H=3.89,N=4.91); Found (C=62.94,H=3.80,N=4.59)

6-Hydroxy-2-(3-hydroxybenzoyl)benzothiazole (Compound 19) mp: 249–250° C. (decomp.) $^1$H-NMR (DMSO-d$_6$): 7.13(s,2H,Ar—H), 7.42(dd,J=8.8 Hz,1H,Ar—H), 7.43(dd,J=8.8,6.8 Hz,1H,Ar—H), 7.52(s,1H,Ar—H), 7.80(s,1H,Ar—H), 7.91(d,J=6.8 Hz,1H,Ar—H), 8.09(d,J=8.8 Hz,1H,Ar—H), 9.91(brs,1H,OH), 10.39(brs,1H,OH) IR(KBr) cm$^{-1}$: 3388(OH), 3286(OH), 1585(C=O), 1489, 1456, 1238 MS m/z: 271(M$^+$) Elementary analysis (C$_{14}$H$_9$NO$_3$S 0.1 H$_2$O): Calculated (C=61.57,H=3.40,N=5.13); Found (C=61.58,H=3.45,N=5.10)

2-(4-Bromobenzoyl)-6-methoxybenzothiazole (Compound 20) mp: 190–190.5° C. $^1$H-NMR(DMSO-d$_6$): 3.90(s,3H,CH$_3$), 7.28(d,J=9.0 Hz,1H,Ar—H), 7.82–7.89(m, 3H,Ar—H), 8.17(d,J=9.0 Hz,1H,Ar—H), 8.38(d,J=8.2 Hz,2H,Ar—H) IR(KBr) cm$^{-1}$: 1637(C=O), 1605, 1585, 1497, 1481, 1257, 1230 MS m/z: 349(M$^{+,81}$Br), 347(M$^+$, $^{79}$Br) Elementary analysis (C$_{15}$H$_{10}$BrNO$_2$S): Calculated (C=51.74,H=2.89,N=4.02); Found (C=51.46,H=2.80,N=3.82)

2-(4-Bromobenzoyl)-6-hydroxybenzothiazole (Compound 21) mp: 178–179° C. $^1$H-NMR(DMSO-d$_6$): 7.15(dd,J=8.8,2.0 Hz,1H,Ar—H), 7.53(d,J=2.0 Hz,1H,Ar—H), 7.86(d,J=8.6 Hz,2H,Ar—H), 8.09(d,J=8.8 Hz,1H,Ar—H), 8.37(d,J=8.6 Hz,2H,Ar—H), 10.43(brs,1H,OH) IR(KBr) cm$^{-1}$: 3340(OH), 1620, 1603(C=O), 1479, 1236 MS m/z: 335(M$^{+,81}$Br), 333(M$^{+,79}$Br) Elementary analysis (C$_{14}$H$_8$BrNO$_2$S): Calculated (C=50.32,H=2.41,N=4.20); Found (C=50.08,H=2.45,N=4.13)

6-Hydroxy-2-(2-hydroxybenzoyl)benzothiazole (Compound 22) mp: 173–175° C. $^1$H-NMR(DMSO-d$_6$): 7.02(d,J=6.4 Hz,2H,Ar—H), 7.12(d,J=8.8 Hz,1H,Ar—H), 7.49–7.59(m,2H,Ar—H), 8.06(d,J=8.8 Hz,1H,Ar—H), 8.36 (d,J=7.8 Hz,1H,Ar—H), 10.43(brs,1H,OH), 10.99(brs,1H, OH) IR(KBr) cm$^{-1}$: 3417(OH), 3385(OH), 1622(C=O), 1589, 1487, 1468, 1240 MS m/z: 271(M$^+$) Elementary analysis (C$_{14}$H$_9$NO$_3$S): Calculated (C=61.98,H=3.34,N=5.16); Found (C=61.75,H=3.28,N=5.04)

2-(2-Chlorobenzoyl)-6-hydroxybenzothiazole (Compound 23) mp: 172–173° C. $^1$H-NMR(DMSO-d$_6$):

7.12(d,J=8.0 Hz,1H,Ar—H), 7.54(brs,2H,Ar—H), 7.63(s, 2H,Ar—H), 7.77(d,J=6.4 Hz,1H,Ar—H), 8.01(d,J=8.0 Hz,1H,Ar—H), 10.43(brs,1H,OH), 10.99(brs,1H,OH) IR(KBr) cm$^{-1}$: 3459(OH), 1648(C=O), 1601, 1485, 1255 MS m/z: 291(M$^-$,Cl), 289(M$^+$,$^{35}$Cl) Elementary analysis ($C_{14}H_8ClNO_2S$ 0.1 $H_2O$): Calculated (C=57.68,H=2.83,N= 4.80); Found (C=57.66,H=2.78,N=4.58)

2-(3-Chlorobenzoyl)-6-hydroxybenzothiazole (Compound 24) mp 156–157° C. $^1$H-NMR(DMSO-d$_6$): 7.15 (d,J=8.6 Hz,1H,Ar—H), 7.53(s,1H,Ar—H), 7.67(dd,J=8.0, 7.6 Hz,1H,Ar—H), 7.82(d,J=8.0 Hz,1H,Ar—H), 8.12(d,J= 8.6 Hz,1H,Ar—H) 8.36(d,J=7.6 Hz,1H,Ar—H), 8.41(s,1H, Ar—H), 10.45(brs,1H,OH) IR(KBr) cm$^{-1}$: 3456(OH), 1649 (C=O), 1601, 1483, 1255 MS m/z: 291(M$^+$,$^{37}$Cl), 289(M$^+$, $^{35}$Cl) Elementary analysis ($C_{14}H_8ClNO_2S$): Calculated (C=58.04,H=2.78,N=4.83); Found (C=58.34,H=2.78,N= 4.43)

2-(4-Chlorobenzoyl)-6-hydroxybenzothiazole (Compound 25) mp: 177–177.5° C. $^1$H-NMR(DMSO-d$_6$): 6.64(dd,J=9.0,2.2 Hz,1H,Ar—H), 7.54(d,J=2.2 Hz,1H,Ar—H), 7.71(d,J=8.8 Hz,2H,Ar—H), 8.10(d,J=9.0 Hz,1H,Ar—H), 8.46(d,J=8.8 Hz,2H,Ar—H), 10.43(brs,1H,OH) IR(KBr) cm$^{-1}$: 3396(OH), 1622, 1603(C=O), 1483, 1259, 1234 MS m/z: 291(M$^+$,$^{37}$Cl), 289(M$^+$,$^{35}$Cl) Elementary analysis ($C_{14}H_8ClNO_2S$): Calculated (C=58.04,H=2.78,N= 4.83); Found (C=58.34,H=2.90,N=4.55)

6-Hydroxy-2-(2-methylbenzoyl)benzothiazole (Compound 26) mp: 200–202° C. $^1$H-NMR(DMSO-d$_6$): 2.37(s,3H,CH$_3$), 7.11(d,J=9.2 Hz,1H,Ar—H), 7.34–7.41(m, 2H,Ar—H), 7.49–7.57(m,2H,Ar—H), 7.83(d,J=7.6 Hz,1H, Ar—H), 8.01(d,J=9.0 Hz,1H,Ar—H), 10.41(brs,1H,OH) IR(KBr) cm$^{-1}$: 3410(OH), 1639, 1610(C=O), 1552, 1498, 1468, 1257 MS m/z: 269(M$^+$) Elementary analysis ($C_{15}H_{11}NO_2S$ 0.1 EtOH): Calculated (C=66.65,H=4.27,N= 5.11); Found (C=67.07,H=4.21,N=4.68)

6-Hydroxy-2-(3-methylbenzoyl)benzothiazole (Compound 27) mp: 170–171° C. $^1$H-NMR(DMSO-d$_6$): 2.44(s,3H,CH$_3$), 7.14(d,J=8.6 Hz,1H,Ar—H), 7.46–7.60(m, 3H,Ar—H), 8.10(d,J=8.6 Hz,1H,Ar—H), 8.15(s,1H,Ar—H), 8.25(d,J=7.0 Hz,1H,Ar—H), 10.43(brs,1H,OH) IR(KBr) cm$^{-1}$: 3407(OH), 1603(C=O), 1595, 1487, 1233, 1198 MS m/z: 269(M$^+$)

6-Hydroxy-2-(4-methylbenzoyl)benzothiazole (Compound 28) mp: 186–187° C. $^1$H-NMR(DMSO-d$_6$): 2.44(s,3H,CH$_3$), 7.14(dd,J=9.0,2.4 Hz,1H,Ar—H), 7.44(d, J=8.2 Hz,2H,Ar—H), 7.52(d,J=2.4 Hz,1H,Ar—H), 8.09(d, J=9.0 Hz,1H,Ar—H), 8.37(d,J=8.2 Hz,2H,Ar—H), 10.38 (brs,1H,OH) IR(KBr) cm$^{-1}$: 3398(OH), 1635, 1605, 1558, 1492, 1259 MS m/z: 269(M$^+$) Elementary analysis ($C_{15}H_{11}NO_2S$): Calculated (C=66.90,H=4.12,N=5.20); Found (C=67.31,H=4.07,N=4.77)

2-(3-Chloro-4-hydroxybenzoyl)-6-hydroxybenzothiazole (Compound 29) mp: 225–226° C. $^1$H-NMR(DMSO-d$_6$): 7.13(dd,J=9.0,2.2 Hz,1H,Ar—H), 7.18(d,J=8.6 Hz,1H,Ar—H), 7.51(d,J=2.2 Hz,1H,Ar—H), 8.10(d,J=9.0 Hz,1H,Ar—H), 8.38(dd,J=8.6,2.2 Hz,1H,Ar—H), 8.59(d,J=2.0 Hz,1H, Ar—H), 10.36(brs,1H,OH), 11.50(brs,1H,OH) IR(KBr) cm$^{-1}$: 3408(OH), 1593(C=O), 1487, 1252 MS m/z: 307 (M$^+$,$^{37}$Cl), 305(M$^+$,$^{±}$Cl) Elementary analysis ($C_{14}H_8ClNO_3S$ 0.1 $H_2O$): Calculated (C=54.68,H=2.69,N= 4.55); Found (C=54.51,H=2.70,N=4.55)

6-Hydroxy-2-(4-methoxycarbonylbenzoyl)benzothiazole (Compound 30) mp: 205–206° C. $^1$H-NMR(DMSO-d$_6$) 3.92 (s,3H,CH$_3$), 7.15(dd,J=9.0,2.4 Hz,1H,Ar—H), 7.54(d,J=2.4 Hz,1H,Ar—H), 8.10(d,J=9.0 Hz,1H,Ar—H), 8.17(d,J=8.4 Hz,2H,Ar—H), 8.49(d,J=8.4 Hz,2H,Ar—H), 10.50(brs,1H, OH) IR(KBr) cm$^{-1}$: 3394(OH), 1705(C=O), 1645(C=O), 1601, 1485, 1230 MS m/z: 313(M$^+$) Elementary analysis ($C_{16}H_{11}NO_4S$): Calculated (C=61.33,H=3.54,N=4.47); Found (C=61.46,H=3.53,N=4.22)

2-[4-(N,N-Dimethylamino)benzoyl]-6-hydroxybenzothiazole (Compound 31) mp: 213–214° C. $^1$H-NMR(DMSO-d$_6$): 3.09(s,6H,CH$_3$), 6.84(d,J=8.6 Hz,2H, Ar—H), 7.11(d,J=8.6 Hz,1H,Ar—H), 7.48(s,1H,Ar—H), 8.05(d,J=8.6 Hz,1H,Ar—H), 8.48(d,J=8.6 Hz,2H,Ar—H), 10.28(brs,1H,OH) IR(KBr) cm$^{-1}$: 3423(OH), 1603(C=O), 1576, 1489, 1196 MS m/z: 298(M$^+$) Elementary analysis ($C_{16}H_{14}N_2O_2S$ ⅓ $H_2O$): Calculated (C=63.14,H=4.86,N= 9.20); Found (C=62.96,H=4.87,N=8.97)

6-Hydroxy-2-(2-hydroxy-3-methoxybenzoyl) benzothiazole (Compound 32) mp: 227–228° C. $^1$H-NMR (DMSO-d$_6$): 3.85(s,3H,CH$_3$), 6.96(dd,J=9.0,8.0 Hz,1H, Ar—H), 7.12(d,J=8.0 Hz,1H,Ar—H), 7.26(d,J=8.0 Hz,1H, Ar—H), 7.51(s,1H,Ar—H), 7.87(d,J=7.8 Hz,1H,Ar—H), 8.05(d,J=9.0 Hz,1H,Ar—H), 10.63(brs,1H,OH) IR(KBr) cm$^{-1}$: 3439(OH), 1618(C=O), 1454, 1254, 1249 MS m/z: 301(M$^+$) Elementary analysis ($C_{15}H_{11}NO_4S$ 0.2 $H_2O$): Calculated (C=59.09,H=3.77,N=4.59); Found (C=59.26,H= 3.73,N=4.27)

6-Hydroxy-2-(4-hydroxy-3-methoxybenzoyl) benzothiazole (Compound 33) mp: 212–213° C. $^1$H-NMR (DMSO-d$_6$): 3.88(s,3H,CH$_3$), 6.99(d,J=8.4 Hz,1H,Ar—H), 7.13(d,J=8.0 Hz,1H,Ar—H), 7.50(s,1H,Ar—H), 8.00(s,1H, Ar—H), 8.08(d,J=8.0 Hz,1H,Ar—H), 8.29(d,J=8.4 Hz,1H, Ar—H), 10.33(brs,1H,OH) IR(KBr) cm$^{-1}$: 3386(OH), 3251 (OH), 1605(C=O), 1489, 1281, 1234 MS m/z: 300(M$^+$—H) Elementary analysis ($C_{15}H_9NO_4S$ 0.9 $H_2O$): Calculated (C=56.74,H=4.06,N=4.41); Found (C=56.93,H=3.96,N= 4.40)

6-Hydroxy-2-(3-hydroxy-4-methoxybenzoyl) benzothiazole (Compound 34) mp: 219–220.5° C. $^1$H-NMR (DMSO-d$_6$): 3.90(s,3H,CH$_3$), 7.13(d,J=8.6 Hz,1H,Ar—H), 7.15(d,J=8.8 Hz,1H,Ar—H), 7.49(s,1H,Ar—H), 7.89(s,1H, Ar—H), 8.08(d,J=8.8 Hz,1H,Ar—H), 8.19(d,J=8.6 Hz,1H, Ar—H), 9.57(brs,1H,OH), 10.33(brs,1H,OH) IR(KBr) cm$^{-1}$: 3386(OH), 1605(C=O), 1489, 1273, 1225 MS m/z: 301(M$^+$) Elementary analysis ($C_{15}H_9NO_4S$ 0.5 $H_2O$): Calculated (C=58.06,H=3.89,N=4.51); Found (C=57.86,H= 3.81,N=4.37)

6-Hydroxy-2-(3-Chloro-4-methoxybenzoyl) benzothiazole (Compound 35) mp: 232–234° C. $^1$H-NMR (DMSO-d$_6$): 4.01(s,3H,CH$_3$), 7.14(d,J=8.4 Hz,1H,Ar—H), 7.39(d,J=8.8 Hz,1H,Ar—H), 7.51(s,1H,Ar—H), 8.11(d,J= 8.8 Hz,1H,Ar—H), 8.54(d,J=8.4 Hz,1H,Ar—H), 8.56(s,1H, Ar—H), 10.40(brs,1H,OH) IR(KBr) cm$^{-1}$: 3363(OH), 1599 (C=O), 1578, 1483, 1282, 1228 MS m/z: 321(M$^+$,$^{37}$Cl), 319(M$^+$,$^{35}$Cl) Elementary analysis ($C_{15}H_{10}ClNO_3S$): Calculated (C=56.34,H=3.15,N=4.38); Found (C=56.49,H= 3.18,N=4.12)

6-Hydroxy-2-(4-hydroxymethylbenzoyl)benzothiazole (Compound 36) mp: 209–210° C. $^1$H-NMR(DMSO-d$_6$): 4.64(s,2H,CH$_2$), 5.43(s,1H,OH), 7.14(d,J=7.4 Hz,1H,Ar—H), 7.50–7.58(m,3H,Ar—H), 8.10(d,J=7.4 Hz,1H,Ar—H), 8.41(d,J=6.8 Hz,1H,Ar—H), 10.39(brs,1H,OH) IR(KBR) cm$^{-1}$: 3423(OH), 3265(OH), 1603(C=O), 1483, 1221 MS m/z: 285(M$^+$) Elementary analysis ($C_{15}H_{11}NO_3S$): Calculated (C=63.14,H=3.89,N=4.91); Found (C=63.27,H=3.86, N=4.65)

2-(4-Fluorobenzoyl)-6-hydroxybenzothiazole (Compound 37) mp: 179–180° C. $^1$H-NMR(DMSO-d$_6$): 7.15(d,J=8.6 Hz,1H,Ar—H), 7.47(t,J=8.2 Hz,2H,Ar—H), 7.53(s,1H,Ar—H), 8.10(d,J=8.6 Hz,1H,Ar—H), 8.55(s,2H, Ar—H), 10.42(brs,1H,OH) IR(KBr) cm$^{-1}$: 3348(OH), 1626 (C=O), 1599, 1489, 1258, 1161 MS m/z: 273(M$^{30}$) Elementary analysis (C$_{14}$H$_8$FNO$_2$S): Calculated (C=61.53, H=2.95,N=5.13); Found (C=61.39,H=3.23,N=4.90)

6-Hydroxy-2-(3-methoxybenzoyl)benzothiazole (Compound 38) mp: 166–167° C. $^1$H-NMR(DMSO-d$_6$): 3.87(s,3H,CH$_3$), 7.15(d,J=8.8 Hz,1H,Ar—H), 7.33(t,J=7.2 Hz,1H,Ar—H), 7.52(s,1H,Ar—H), 7.55(dd,J=7.6,7.2 Hz,1H,Ar—H), 7.94(s,1H,Ar—H), 8.06(d,J=7.6 Hz,1H, Ar—H), 8.11(d,J=8.8 Hz,1H,Ar—H), 10.41(brs,1H,OH) IR(KBr) cm$^{-1}$: 3383(OH), 1595(C=O), 1471, 1263 MS m/z: 285(M$^+$) Elementary analysis (C$_{15}$H$_{11}$NO$_3$S 0.1 H$_2$O): Calculated (C=62.74,H=3.93,N=4.88); Found (C=62.55,H=3.77,N=4.57)

6-Hydroxy-2-(2-methoxybenzoyl)benzothiazole (Compound 39) mp: 184.5–185.5° C. $^1$H-NMR(DMSO-d$_6$) 3.73(s,3H,CH$_3$), 7.06–7.14(m,2H,Ar—H), 7.22(d,J=7.8 Hz,1H,Ar—H), 7.51(s,1H,Ar—H), 7.56–7.63(m,3H,Ar—H), 7.97(d,J=8.8 Hz,1H,Ar—H), 10.36(brs,1H,OH) IR(KBr) cm$^{-1}$: 3421(OH), 1627(C=O), 1610, 1554, 874 MS m/z: 285(M$^+$) Elementary analysis (C$_{15}$H$_{11}$NO$_3$S 0.1 H$_2$O): Calculated (C=62.74,H=3.93,N=4.88); Found (C=62.92,H=3.88,N=4.49)

2-(4-Acetoxybenzoyl)-6-hydroxybenzothiazole (Compound 40) mp: 176–177° C. $^1$H-NMR(DMSO-d$_6$) 2.34 (s,3H,CH$_3$), 7.12(dd,J=9.0,2.0 Hz,1H,Ar—H), 7.40(d,J=8.6 Hz,2H,Ar—H), 7.53(d,J=2.0 Hz,1H,Ar—H), 8.11(d,J=9.0 Hz,1H,Ar—H), 8.49(d,J=8.6 Hz,2H,Ar—H), 10.41(brs,1H, OH) IR(KBr) cm$^{-1}$: 3379(OH), 1767(C=O), 1601(C=O), 1483, 1254, 1198 MS m/z: 313(M$^+$) Elementary analysis (C$_{16}$H$_{11}$NO$_4$S 0.1 H$_2$O): Calculated (C=60.98,H=3.58,N=4.44); Found (C=61.11,H=3.55,N=4.09)

2-(4-Acetamidobenzoyl)-6-hydroxybenzothiazole (Compound 41) mp: 190–191° C. (decomp.) $^1$H-NMR (DMSO-d$_6$): 2.12(s,3H,CH$_3$), 7.14(d,J=9.0 Hz,1H,Ar—H), 7.51(s,1H,Ar—H), 7.81(d,J=8.6 Hz,2H,Ar—H), 8.10(d,J=9.0 Hz,1H,Ar—H), 8.48(d,J=8.6 Hz,2H,Ar—H), 10.36(brs, 1H,OH), 10.40(s,1H,NH) IR(KBr) cm$^{-1}$: 3400(OH), 3271 (NH), 1678(C=O), 1622(C=O), 1581, 1498, 1261 MS m/z: 312(M$^+$) Elementary analysis (C$_{16}$H$_{12}$N$_2$O$_3$S 0.2 EtOH): Calculated (C=61.26,H=3.96,N=8.38); Found (C=61.54,H=3.96,N=8.38)

2-(4-t-Butylbenzoyl)-6-hydroxybenzothiazole (Compound 42) mp: 168–169° C. $^1$H-NMR(DMSO-d$_6$): 1.35(s,9H,CH$_3$), 7.14(dd,J=9.0,2.0 Hz,1H,Ar—H), 7.52(d, J=2.0 Hz,1H,Ar—H), 7.65(d,J=8.4 Hz,2H,Ar—H), 8.08(d, J=9.0 Hz,1H,Ar—H), 8.37(d,J=8.4 Hz,2H,Ar—H), 10.39 (brs,1H,OH) IR(KBr) cm$^{-1}$: 3219(OH), 2962, 1632(C=O), 1606, 1552, 1488, 1257 MS m/z: 311(M$^+$) Elementary analysis (C$_{18}$H$_{17}$NO$_2$S): Calculated (C=69.43,H=5.50,N=4.50); Found (C=69.46,H=5.63,N=4.31)

2-(3,4-Diacetoxybenzoyl)-6-hydroxybenzothiazole (Compound 43) mp: 145–146° C. $^1$H-NMR(DMSO-d$_6$): 2.35(s,3H,CH$_3$), 2.50(s,3H,CH$_3$), 7.15(dd,J=9.0,2.4 Hz,1H, Ar—H), 7.53(d,J=2.4 Hz,1H,Ar—H), 7.56(d,J=8.6 Hz,1H, Ar—H), 8.11(d,J=9.0 Hz,1H,Ar—H), 8.28(d,J=2.0 Hz,1H, Ar—H), 8.44(dd,J=8.6,2.0 Hz,1H,Ar—H), 10.46(brs,1H, OH) IR(KBr) cm$^{-1}$: 3356(OH), 1770(C=O), 1730(C=O), 1643(C=O), 1603, 1489, 1373, 1211 MS m/z: 371(M$^+$) Elementary analysis (C$_{18}$H$_{13}$NO$_6$S): Calculated (C=58.22, H=3.53,N=3.77); Found (C=58.45,H=3.68,N=3.56)

6-Hydroxy-2-(4-iso-propylbenzoyl)benzothiazole (Compound 44) mp: 108–110° C. $^1$H-NMR(DMSO-d$_6$): 1.27(d,J=6.8 Hz,6H,CH$_3$), 2.97–3.07(m,1H,CH), 7.14(dd,J=9.0,2.2 Hz,1H,Ar—H), 7.47–7.53(m,3H,Ar—H), 8.09(d,J=9.0 Hz,1H,Ar—H), 8.37(d,J=8.2 Hz,2H,Ar—H), 10.39(brs, 1H,OH) IR(KBr) cm$^{-1}$: 3362(OH), 2958, 1599(C=O), 1487, 1259 MS m/z: 297(M$^+$) Elementary analysis (C$_{17}$H$_{15}$NO$_2$S): Calculated (C=68.66,H=5.08,N=4.71); Found (C=68.97,H=5.21,N=4.50)

6-Hydroxy-2-(4-trifluoromethylbenzoyl)benzothiazole (Compound 45) mp: 183–184° C. (decomp.) $^1$H-NMR (DMSO-d$_6$): 7.15(d,J=9.0 Hz,1H,Ar—H), 7.54(s,1H,Ar—H), 8.01(d,J=8.0 Hz,2H,Ar—H), 8.10(d,J=9.0 Hz,1H,Ar—H), 8.54(d,J=8.0 Hz,2H,Ar—H), 10.47(brs,1H,OH) IR(KBr) cm$^{-1}$: 3431(OH), 1668(C=O), 1602, 1483, 1319, 1227 MS m/z: 323(M$^+$) Elementary analysis (C$_{15}$H$_8$F$_3$NO$_2$S 0.25 H$_2$O): Calculated (C=54.96,H=2.61,N=4.27); Found (C=55.31,H=2.47,N=3.90)

tert-Butyl 4-(6-hydroxy-2-benzothiazolecarbonyl) phenoxy-acetate (Compound 46) mp: 156–157° C. $^1$H-NMR (DMSO-d$_6$): 1.47(s,9H,CH$_3$), 4.85(s,2H,CH$_2$), 7.13–7.16 (m,3H,Ar—H), 7.52(d,J=2.4 Hz,1H,Ar—H), 8.10(d,J=9.0 Hz,1H,Ar—H), 8.51(d,J=9.0 Hz,2H,Ar—H), 10.42(brs,1H, OH) IR(KBr) cm$^{-1}$: 3442(OH), 1755(C=O), 1736, 1601 (C=O), 1489, 1228 MS m/z: 385(M$^+$) Elementary analysis (C$_{20}$H$_{19}$NO$_5$S): Calculated (C=62.32,H=4.97,N=3.63); Found (C=62.28,H=4.90,N=3.93)

4-(6-Hydroxy-2-benzothiazolecarbonyl)phenoxyacetic Acid (Compound 47) mp: 216–217° C. $^1$H-NMR(DMSO-d$_6$): 4.86(s,2H,CH$_2$), 7.29(dd,J=9.2,2.4 Hz,1H,Ar—H), 7.87 (d,J=2.4 Hz,1H,Ar—H), 8.18(d,J=9.0 Hz,1H,Ar—H), 8.44 (d,J=8.6 Hz,2H,Ar—H), 8.58(d,J=8.6 Hz,2H,Ar—H), 10.37 (brs,1H,OH), 13.13(brs,1H,COOH) IR(KBr) cm$^{-1}$: 3413 (OH), 3074(OH), 1772(C=O), 1601(C=O), 1491, 1257 MS m/z: 329(M$^+$) Elementary analysis (C$_{16}$H$_{11}$NO$_5$S 0.5 H$_2$O): Calculated (C=56.80,H=3.57,N=4.14); Found (C=56.73,H=3.50,N=4.26)

6-Methoxy-2-(4-nitrobenzoyl)benzothiazole (Compound 48) mp: 225–226° C. (decomp.) $^1$H-NMR(DMSO-d$_6$): 3.91 (s,3H,CH$_3$), 7.14(dd,J=9.0,2.2 Hz,1H,Ar—H), 7.47–7.53 (m,3H,Ar—H), 8.09(d,J=9.0 Hz,1H,Ar—H), 8.37(d,J=8.2 Hz,2H,Ar—H) IR(KBr) cm$^{-1}$: 1641(C=O), 1601, 1525 (NO$_2$), 1354(NO$_2$) MS m/z: 314(M$^+$) Elementary analysis (C$_{15}$H$_{10}$N$_2$O$_4$S): Calculated (C=57.32,H=3.21,N=8.91); Found (C=57.16,H=3.13,N=9.25)

6-Methoxy-2-(3-nitrobenzoyl) benzothiazole (Compound 49) mp: 156–157° C. (decomp.) $^1$H-NMR (DMSO-d$_6$): 3.92 (s,3H,CH$_3$), 7.29(dd,J=9.2,2.6 Hz,1H,Ar—H), 7.87(d,J=2.6 Hz,1H,Ar—H), 7.94(dd,J=9.2,9.0 Hz,1H,Ar—H), 8.20(d,J=9.0 Hz,1H,Ar—H), 8.58(dd,J=8.2,2.0 Hz,1H,Ar—H), 8.81 (d,J=7.8 Hz,1H,Ar—H), 9.21(d,J=2.0 Hz,1H,Ar—H) IR(KBr) cm$^{-1}$: 1647(C=O), 1603, 1527(NO$_2$), 1941, 1356 (NO$_2$) MS m/z: 314(M$^+$) Elementary analysis (C$_{15}$H$_{10}$N$_2$O$_4$S): Calculated (C=57.32,H=3.21,N=8.91); Found (C=57.28,H=3.29,N=9.07)

2-(3-Fluorobenzoyl)-6-hydroxybenzothiazole (Compound 50) mp: 162–163° C. (decomp.) $^1$H-NMR (DMSO-d$_6$): 7.15(d,J=8.6 Hz,1H,Ar—H), 7.53(s,1H,Ar—H), 7.36(dd,J=7.2,7.2 Hz,1H,Ar—H), 7.69(dd,J=7.2,6.2 Hz,1H,Ar—H), 8.12(d,J=8.6 Hz,1H,Ar—H), 8.21(d,J=9.2 Hz,1H,Ar—H), 8.27(d,J=7.2 Hz,1H,Ar—H), 10.44(brs,1H, OH) IR(KBr) cm$^{-1}$: 3433(OH), 1629(C=O), 1581, 1482, 1256, 841 MS m/z: 273(M$^+$)

2-[3-t-Butyl-4-(2-methoxyethoxy)methoxy]benzoyl-6-(2-methoxyethoxy)methoxybenzothiazole (Compound 51) $^1$H-NMR(DMSO-d$_6$): 1.45(s,9H,CH$_3$), 3.30–3.42(m,6H, CH$_3$), 3.55–3.64(m,4H,CH$_2$), 5.38(s,2H,CH$_2$), 5.44(s,2H, CH$_2$), 7.22–7.32(m,3H,Ar—H), 7.67(d,J=2.4 Hz,1H,Ar—H), 8.09(d,J=9.0 Hz,1H,Ar—H), 8.53(d,J=7.0 Hz,1H,Ar—H) IR(neat) cm$^{-1}$: 2925, 1637(C=O), 1592, 1489, 1216

5-Trifluoromethyl-2-(4-hydroxybenzoyl)benzothiazole (Compound 52) mp: 234.5–236° C. $^1$H-NMR(DMSO-d$_6$):

6.99(d,J=8.8 Hz,2H,Ar—H), 7.95(d,J=8.4 Hz,1H,Ar—H), 8.50(d,J=8.8 Hz,2H,Ar—H), 8.52(d,J=8.4 Hz,1H,Ar—H), 8.66(s,1H,Ar—H), 10.81(brs,1H,OH) IR(KBr) cm$^{-1}$: 3275 (OH), 1622(C=O), 1566, 1491, 1323, 1292, 1174, 1122 MS m/z: 323(M$^+$)

6-Chloro-2-(4-hydroxybenzoyl)benzothiazole (Compound 53) mp: 209–210° C. $^1$H-NMR(DMSO-d$_6$): 6.97(d,J=8.8 Hz,2H,Ar—H), 7.70(dd,J=8.8,2.0 Hz,1H,Ar—H), 8.28(d,J=8.8 Hz,1H,Ar—H), 8.44(d,J=2.0 Hz,1H,Ar—H), 8.47(d,J=8.8 Hz,2H,Ar—H), 10.80(brs,1H,OH) IR(KBr) cm$^{-1}$: 3383(OH), 1605(C=O), 1572, 1485, 1300, 1134 MS m/z: 291(M$^+$,$^{37}$Cl), 289(M$^+$,$^{35}$Cl) Elementary analysis (C$_{14}$H$_8$ClNO$_2$S): Calculated (C=58.04,H=2.78,N=4.83); Found (C=58.20,H=2.68,N=5.09)

6-Acetamido-2-(4-hydroxybenzoyl)benzothiazole (Compound 54) mp: 226–227° C. $^1$H-NMR(DMSO-d$_6$): 2.13(s,3H,CH$_3$), 6.85(dd,J=8.8 Hz,2H,Ar—H), 7.76(d,J=9.0 Hz,Ar—H), 8.17(d,J=9.0 Hz,1H,Ar—H), 8.43(d,J=8.8 Hz,2H,Ar—H), 8.62(s,1H,Ar—H), 10.39(brs,1H,OH) IR(KBr) cm$^{-1}$: 3323(OH), 3155(NH), 1678(C=O), 1601 (C=O), 1572, 1514, 1489, 1296 MS m/z: 312(M$^+$)

5-Chloro-2-(4-hydroxybenzoyl)benzothiazole (Compound 55) mp: 223–225° C. (decomp.) $^1$H-NMR (DMSO-d$_6$): 6.98(d,J=8.6 Hz,2H,Ar—H), 7.70(d,J=8.4 Hz,1H,Ar—H), 8.31(d,J=8.4 Hz,1H,Ar—H), 8.39(s,1H, Ar—H), 8.47(d,J=8.6 Hz,2H,Ar—H), 10.79(brs,1H,OH) IR(KBr) cm$^{-1}$: 3323(OH), 1606(C=O), 1597, 1562, 1489, 1302, 1124 MS m/z: 291(M$^+$,$^{37}$Cl), 289(M$^+$,$^{35}$Cl) Elementary analysis (C$_{14}$H$_8$ClNO$_2$S): Calculated (C=58.04,H=2.78,N=4.83); Found (C=58.31,H=3.14,N=4.93)

2-(4-Hydroxybenzoyl)-6-methylbenzothiazole (Compound 56) mp: 210–212° C. $^1$H-NMR(DMSO-d$_6$): 2.51(s,3H,CH$_3$), 6.98(d,J=8.4 Hz,2H,Ar—H), 7.48(d,J=8.2 Hz,1H,Ar—H), 8.03(s,1H,Ar—H), 8.15(d,J=8.2 Hz,1H, Ar—H), 8.48(d,J=8.4 Hz,2H,Ar—H), 10.71(brs,1H,OH) IR(KBr) cm$^{-1}$: 3333(OH), 1628, 1597(C=O), 1491, 1299, 1170 MS m/z: 269(M$^+$) Elementary analysis (C$_{15}$H$_{11}$NO$_2$S): Calculated (C=66.90,H=4.12,N=5.20); Found (C=66.85,H=4.16,N=5.05)

2-(4-Hydroxybenzoyl)-4-methylbenzothiazole (Compound 57) mp: 186–187° C. (decomp.) $^1$H-NMR (DMSO-d$_6$): 2.51(s,3H,CH$_3$), 6.98(d,J=8.4 Hz,2H,Ar—H), 7.48(d,J=8.2 Hz,1H,Ar—H), 8.03(s,1H,Ar—H), 8.15(d,J=8.2 Hz,1H,Ar—H), 8.48(d,J=8.4 Hz,2H,Ar—H), 10.71(brs, 1H,OH) IR(KBr) cm$^{-1}$: 3348(OH), 1627, 1579(C=O), 1488, 1296, 1171, 1117 MS m/z: 269(M$^+$) Elementary analysis (C$_{15}$H$_{11}$NO$_2$S): Calculated (C=66.90,H=4.12,N=5.20); Found (C=67.12,H=4.16,N=5.36)

4-Hydroxy-2-(4-hydroxybenzoyl)benzothiazole (Compound 58) mp: 213–214° C. $^1$H-NMR(DMSO-d$_6$): 6.96–7.02(m,3H,Ar—H), 7.45(t,J=7.2,7.2 Hz,1H,Ar—H), 8.58(d,J=7.2 Hz,1H,Ar—H), 8.59(d,J=7.2 Hz,2H,Ar—H), 10.62(brs,2H,OH) IR(KBr) cm$^{-1}$: 3397(OH), 3267(OH), 1616, 1603(C=O), 1569, 1470, 1282 MS m/z: 271(M$^+$)

2-(4-Hydroxybenzoyl)-4-methoxybenzothiazole (Compound 59) mp: 209–210° C. (decomp.) $^1$H-NMR (DMSO-d$_6$): 4.04(s,3H,CH$_3$), 6.98(d,J=7.0 Hz,2H,Ar—H), 7.17(d,J=7.2 Hz,1H,Ar—H), 7.58(dd,J=8.2,7.2 Hz,1H,Ar—H), 7.76(d,J=8.2 Hz,1H,Ar—H), 8.78(d,J=8.2 Hz,2H,Ar—H), 10.72(brs,1H,OH) IR(KBr) cm$^{-1}$: 3407(OH), 1638 (C=O), 1580, 1570, 1566, 1301, 1115, 901 MS m/z: 285 (M$^+$)

4-Chloro-2-(4-hydroxybenzoyl)benzothiazole (Compound 60) mp: 242–243° C. (decomp.) $^1$H-NMR (DMSO-d$_6$): 7.00(d,J=8.8 Hz,2H,Ar—H), 7.63(dd,J=8.2,8.6 Hz,1H,Ar—H), 7.78(dd,J=7.6,0.8 Hz,1H,Ar—H), 8.24(dd, J=8.2,0.8 Hz,1H,Ar—H), 8.52(d,J=8.8 Hz,2H,Ar—H), 10.72(brs,1H,OH) IR(KBr) cm$^{-1}$: 3341(OH), 1597(C=O), 1566, 1492, 1179, 895, 762 MS m/z: 291(M$^+$,$^{37}$Cl), 289 (M$^+$,$^{35}$Cl)

6-Fluoro-2-(4-hydroxybenzoyl)benzothiazole (Compound 61) mp: 174–175° C. $^1$H-NMR(DMSO-d$_6$): 6.99(d,J=8.8 Hz,2H,Ar—H), 7.56(ddd,J=9.0,8.8,2.6 Hz,1H, Ar—H), 8.18(dd,J=8.8,2.6 Hz,1H,Ar—H), 8.33(dd,J=9.0, 5.0 Hz,1H,Ar—H), 8.49(d,J=8.8 Hz,2H,Ar—H), 10.74(brs, 1H,OH) IR(KBr) cm$^{-1}$: 3364(OH), 1625, 1594(C=O), 1491, 1301, 1245, 871 MS m/z: 273(M$^+$)

6-Methoxy-2-(4-methoxycarbonylbenzoyl)benzothiazole (Compound 62) mp: 189.5–190° C. $^1$H-NMR(DMSO-d$_6$): 3.91(s,3H,CH$_3$), 3.93(s,3H,CH$_3$), 7.28(d,J=8.0 Hz,1H,Ar—H), 7.86(s,1H,Ar—H), 8.06(d,J=8.0 Hz,1H,Ar—H), 8.18(d, J=7.6 Hz,2H,Ar—H), 8.50(d,J=7.6 Hz,2H,Ar—H) IR(KBr) cm$^{-1}$: 1727(C=O), 1638(C=O), 1604, 1491, 1229

2-(4-Carboxybenzoyl)-6-methoxybenzothiazole (Compound 63) mp: 260–261° C. (decomp.) $^1$H-NMR (DMSO-d$_6$): 3.91(s,3H,CH$_3$), 7.27(d,J=8.0 Hz,1H,Ar—H), 7.85(s,1H,Ar—H), 8.13(d,J=7.6 Hz,2H,Ar—H), 8.18(d,J= 8.0 Hz,1H,Ar—H), 8.44(d,J=7.6 Hz,2H,Ar—H) IR(KBr) cm$^{-1}$: 3440(OH), 1643(C=O), 1604(C=O), 1491, 1407, 1255, 1228

EXAMPLE 8

Pharmacological actions of the compounds of the present invention for lipid lowering activity were determined by first intravenously administering streptozotocin (45 mg/kg) to Wistar-strain male rats (5 weeks of age). After a week, the rats whose blood glucose levels increased to 240–300 mg/dl were selected and divided uniformly into groups (8 rats/group). The tested drugs (100 mg/kg/day) were orally administered for 3 weeks and blood was collected from the orbita vein. A control group was not administered any compounds of the present invention. Cholesterol, triglyceride and low-density lipoprotein in the blood sample were measured. An example of the results is shown in Table 1. The unit of each value is mg/dl and the standard deviation is also given:

TABLE 1

|  | Control | Compound 7 |
|---|---|---|
| Cholesterol | 956.6 ± 234.4 | 260.8 ± 209.4 |
| Triglyceride | 380.9 ± 161.8 | 161.4 ± 156.5 |
| Low-density lipoprotein | 2988 ± 1387 | 404 ± 708 |

As shown by the above-mentioned results of the pharmacological studies, the benzothiazole derivatives of the present invention have excellent pharmacological activities which significantly decrease cholesterol, triglyceride and low-density lipoprotein in blood. The compounds of the present invention are very useful as medicines such as a remedy for hyperlipemia.

We claim:

1. A benzothiazole derivative represented by the general formula (I) or a pharmaceutically acceptable salt thereof:

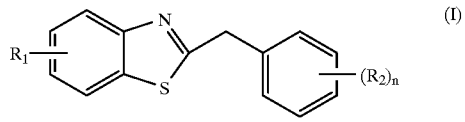

wherein

17

$R_1$ is halogen, trifluoromethyl, acetamido or —$OX_1$;

$X_1$ is hydrogen, alkyl or acyl;

$R_2$ is hydrogen, halogen, alkyl, hydroxyalkyl, trifluoromethyl, nitro, amino which may be substituted with alkyl or acyl, carboxy which may be esterified with alkyl, or —$OX_2$;

$X_2$ is hydrogen, alkyl, acyl, carboxyalkyl which may be esterified with alkyl;

n is an integer from 1 to 3 which denotes the number of substituents $R_2$;

and plural $R_2$ may be the same or different when n is 2 or 3;

with the proviso that $R_1$ is a group other than halogen when $R_2$ is hydrogen.

2. A benzothiazole derivative according to claim 1 wherein $R_1$ is —$OX_1$.

3. A benzothiazole derivative according to claim 2 wherein $X_1$ is hydrogen.

4. A benzothiazole derivative according to claim 2 wherein $X_1$ is alkyl.

5. A benzothiazole derivative according to claim 1 wherein n is 1.

6. A benzothiazole derivative according to claim 5 wherein $R_2$ is —$OX_2$.

7. A benzothiazole derivative according to claim 6 wherein $X_2$ is hydrogen.

8. A benzothiazole derivative according to claim 6 wherein $X_2$ is alkyl.

9. A benzothiazole derivative according to claim 1 wherein $R_1$ is a 6-hydroxyl group.

10. A benzothiazole derivative according to claim 9 wherein $R_2$ is in the 4-position.

11. 2-(4-Hydroxybenzoyl)benzothiazole or a pharmaceutically acceptable salt thereof.

12. A pharmaceutical composition comprising at least one benzothiazole derivative represented by the general formula (I) or a pharmaceutically acceptable salt thereof:

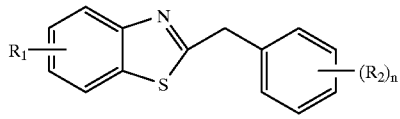
(I)

wherein $R_1$ is halogen, trifluoromethyl, acetamido or —$OX_1$;

$X_1$ is hydrogen, alkyl or acyl;

$R_2$ is hydrogen, halogen, alkyl, hydroxyalkyl, trifluoromethyl, nitro, amino which may be substituted with alkyl or acyl, carboxy which may be esterified with alkyl, or —$OX_2$;

$X_2$ is hydrogen, alkyl, acyl, carboxyalkyl which may be esterified with alkyl;

n is an integer from 1 to 3 which denotes the number of substituents $R_2$;

and plural $R_2$ may be the same or different when n is 2 or 3;

with the proviso that $R_1$ is a group other than halogen when $R_2$ is hydrogen, in a pharmaceutically effective amount with a pharmaceutically acceptable carrier.

13. A lipid lowering composition comprising a lipid lowering amount of at least one benzothiazole derivative represented by the general formula (I) or a pharmaceutically acceptable salt thereof:

18

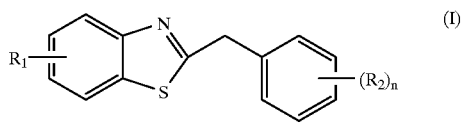
(I)

wherein $R_1$ is halogen, alkyl, trifluoromethyl, acetamido or —$OX_1$;

$X_1$ is hydrogen, alkyl or acyl;

$R_2$ is hydrogen, halogen, alkyl hydroxyalkyl, trifluoromethyl, nitro, amino which may be substituted with alkyl or acyl, carboxy which may be esterified with alkyl, or —$OX_2$;

$X_2$ is hydrogen, alkyl, acyl, carboxyalkyl which may be esterified with alkyl;

n is an integer from 1 to 3 which denotes the number of substituents $R_2$; and plural $R_2$ may be the same or different when n is 2 or 3;

with the proviso that $R_1$ is a group other than chloro when $R_2$ is hydrogen, and a pharmaceutically acceptable carrier.

14. A method for the treatment of hyperlipemia comprising administering to a patient in need of such treatment a therapeutic amount of a benzothiazole derivative represented by the general formula (I) or a pharmaceutically acceptable salt thereof:

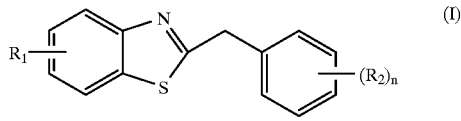
(I)

wherein $R_1$ is halogen, alkyl, trifluoromethyl, acetamido or —$OX_1$;

$X_1$ is hydrogen, alkyl or acyl;

$R_2$ is hydrogen, halogen, alkyl, hydroxyalkyl, trifluoromethyl, nitro, amino which may be substituted with alkyl or acyl, carboxy which may be esterified with alkyl, or —$OX_2$;

$X_2$ is hydrogen, alkyl, acyl, carboxyalkyl which may be esterified with alkyl;

n is an integer from 1 to 3 which denotes the number of substituents $R_2$;

and plural $R_2$ may be the same or different when n is 2 or 3;

with the proviso that $R_1$ is a group other than chloro when $R_2$ is hydrogen.

15. A method for reducing cholesterol, triglyceride or low-density lipoprotein in a patient in need of such reduction comprising administering to said patient a therapeutic amount of at least one benzothiazole derivative represented by the general formula (I) or a pharmaceutically acceptable salt thereof:

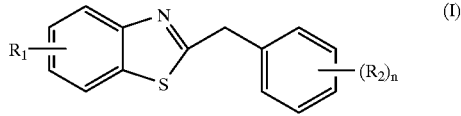
(I)

wherein $R_1$ is halogen, alkyl trifluoromethyl, acetamido or —$OX_1$;

$X_1$ is hydrogen, alkyl or acyl;

$R_2$ is hydrogen, halogen, alkyl, hydroxyalkyl, trifluoromethyl, nitro, amino which may be substituted with alkyl or acyl, carboxy which may be esterified with alkyl, or $-OX_2$;

$X_2$ is hydrogen, alkyl, acyl, carboxyalkyl which may be esterified with alkyl;

n is an integer from 1 to 3 which denotes the number of substituents $R_2$;

and plural $R_2$ may be the same or different when n is 2 or 3;

with the proviso that $R_1$ is a group other than chloro when $R_2$ is hydrogen.

16. A pharmaceutical composition according to claim 12 wherein $R_1$ is $-OX_1$.

17. A lipid lowering composition according to claim 13 wherein $R_1$ is $-OX_1$.

18. A method for the treatment of hvperlipemia according to claim 14 wherein $R_1$ is $-OX_1$.

19. A method for reducing cholesterol, triglyceride, or low-density lipoprotein according to claim 15 wherein $R_1$ is $-OX_1$.

20. A pharmaceutical composition according to claim 12 wherein $R_1$ is a 6-hydroxyl group.

* * * * *